United States Patent
Butsch et al.

(10) Patent No.: US 7,063,713 B1
(45) Date of Patent: Jun. 20, 2006

(54) METHOD FOR SEVERING OR REMOVING A BIOLOGICAL STRUCTURE, ESPECIALLY BONES

(75) Inventors: Michael Butsch, Daisendorf (DE); Rainer Baumgart, Munich (DE)

(73) Assignee: Wittenstein GmbH & Co. KG, Igersheim (DE)

( * ) Notice: Subject to any disclaimer, the term of this patent is extended or adjusted under 35 U.S.C. 154(b) by 0 days.

(21) Appl. No.: 09/890,715

(22) PCT Filed: Dec. 28, 1999

(86) PCT No.: PCT/EP99/10399

§ 371 (c)(1),
(2), (4) Date: Dec. 31, 2001

(87) PCT Pub. No.: WO00/45719

PCT Pub. Date: Aug. 10, 2000

(30) Foreign Application Priority Data

Feb. 5, 1999 (DE) .................. 199 04 640

(51) Int. Cl.
*A61B 17/32* (2006.01)
(52) U.S. Cl. ........................ 606/167; 604/22
(58) Field of Classification Search ........... 606/166, 606/167; 604/22; 451/39, 40, 102, 222; 83/53, 177
See application file for complete search history.

(56) References Cited

U.S. PATENT DOCUMENTS

| | | | | |
|---|---|---|---|---|
| RE33,258 E | * | 7/1990 | Onik et al. ............... | 604/22 |
| 5,259,842 A | * | 11/1993 | Plechinger et al. ........ | 604/152 |
| 5,591,184 A | * | 1/1997 | McDonnell et al. ....... | 606/167 |
| 5,620,414 A | * | 4/1997 | Campbell, Jr. ............ | 604/22 |
| 5,667,102 A | * | 9/1997 | Keller ..................... | 222/95 |
| 5,836,909 A | * | 11/1998 | Cosmescu ................ | 604/35 |
| 5,853,384 A | * | 12/1998 | Bair ........................ | 604/22 |
| 6,066,150 A | * | 5/2000 | Gonon ..................... | 606/167 |
| 6,216,573 B1 | * | 4/2001 | Moutafis et al. ........... | 83/177 |

FOREIGN PATENT DOCUMENTS

EP   258901 A2 *   3/1988

\* cited by examiner

*Primary Examiner*—Eduardo C. Robert
*Assistant Examiner*—D. Jacob Davis
(74) *Attorney, Agent, or Firm*—Bachman & LaPointe, P.C.

(57) ABSTRACT

The invention relates to a method for severing or removing a biological structure, especially bones, by using a water jet cutting device (R) from which a pressurized severing medium (4) is discharged. According to the invention, the severing medium (4) should be projected onto the biological structure in a pulsed manner.

7 Claims, 4 Drawing Sheets

METHOD FOR SEVERING OR REMOVING A BIOLOGICAL STRUCTURE, ESPECIALLY BONES

BACKGROUND OF THE INVENTION

The invention relates to a method of severing or removing a biological structure, in particular bone, having a water-jet cutting system from which a severing medium under high pressure is discharged, and to a cutting-nozzle element and a water-jet cutting system.

Such methods are known on the market and are in use in many different forms and designs. In particular in medicine, it is known to sever, for example from outside, a bone by water-jet cutting. A disadvantage with this is that, in conventional water-jet cutting methods, the soft tissue, and not only the bone, is destroyed. The vascular system in the soft tissue at the bone is important in particular for the knitting of the bone or for the regeneration of the callus. It is therefore necessary during the water-jet removal or severing of biological substances, in particular of bones, to carry out the removal or severing of the bone as carefully as possible. In conventional water-jet cutting methods, the water is applied directly to the exposed bone via a cutting nozzle, in the course of which the vascular system in the bone is also damaged.

An arrangement for cutting by means of a liquid jet has been disclosed by EP 0 636 345 A1, in which arrangement an additional medium is added to a liquid jet by means of vacuum. In this case, pulsing of a liquid jet is produced in a handle, the liquid jet being discharged under pressure losses via an elongated cannula adjoining the handle.

SUMMARY OF THE INVENTION

The object of the present invention is to provide a method and a water-jet cutting system having a cutting-nozzle element with which removal and/or severing of biological substances, in particular of bones, is possible in a simple and careful manner. The ease of manipulation of corresponding water-jet cutting systems having cutting-nozzle element with which removal and/or severing of biological substances, in particular of bones, is possible in a simple and careful manner. The ease of manipulation of corresponding water-jet cutting systems having cutting-nozzle elements is also to be considerably improved. Furthermore, it is the object of the present invention to shorten the operation times, in particular during the severing of bones, in which case high operation costs are to be reduced as a result. In addition, an operation is to carried out with substantially greater care and with a quicker recovery for the patient.

This object is achieved by the severing medium being discharged onto the biological structure in a pulsed manner.

This ensures that, in particular, the soft tissue is moved back by a pulsed jet and then the severing medium strikes the bone in order to partly remove the bone or to sever it. In this case, it may be advantageous to insert a corresponding cutting nozzle for severing the bone into the marrow cavity of the bone and to provide the bone radially with a notch from inside. For example, a radially arranged nozzle in a cutting-nozzle element is rotated in the marrow cavity of a tubular bone during the discharge of the severing medium. In the process, the bone can be severed at least partly from inside. It may possibly also be sufficient to cut only one notch in the bone, so that it can subsequently be severed or pierced in a conventional manner from outside by a small blow. The outer periosteum is not destroyed in the process.

Subsequent further treatment of the bone, for example traction, may then be carried out.

However, it is important that a pulsed water jet is discharged from a nozzle opening of a cutting-nozzle body in a quite specific manner via this method, i.e. at a quite specific frequency and with a pressure change. This pulsation or pulsing is defined as a pressure change of a water jet which undergoes either only a slight pressure change or a complete pressure change up to the absolute pressure drop. A biologically suitable inorganic and/or organic abrasive agent can be fed to the severing medium so that the material-removal capacity is considerably increased during the water-jet cutting. In this way, bones can be severed with substantially lower pressures.

However, it is important that the pulsed discharge of the severing medium results in soft, elastic tissue being moved back upon impingement of the severing medium, whereas the bone tissue is severed or removed when the severing medium impinges on said bone tissue.

Owing to the fact that the severing medium is discharged onto the biological structure in a pulsed manner, and working pressures which would lead to destruction of the softer structures without pulsation are used, and these soft biological structures, on account of their higher elasticity compared with the surrounding harder biological structures, are subjected to lower mechanical loading within the elastic range through suitable selection of the pulsation, the harder biological structures are severed due to the fact that the elasticity or fracture limit is exceeded.

If a cutting-nozzle element is inserted into the bone, a corresponding element, in particular a tube element or the like, is provided in order to draw the discharging medium out of the interior of the bone.

The pulsation is produced in the cutting nozzle essentially by varying cross sections in the cutting-nozzle element itself. This has the advantage that no inertia losses, for example due to long, possibly elastic or resilient, tube lines, would weaken a changing pressure impulse.

So that a corresponding pulsation can be produced in the individual cutting-nozzle elements, a shut-off element sits inside a cutting-nozzle body, this shut-off element influencing a medium, flowing along inside or outside the latter, by a rotational or translatory reciprocating movement. A change of cross section is effected in the process, a pressure change, in particular a pressure drop, is effected. The pressure drop may even approach zero.

However, within the scope of the present invention, it is also intended that the pressure changes can take place within small and also large ranges. There are no limits to the invention in this respect either.

In the preferred exemplary embodiment, a cutting-nozzle element which has at least one radial cutting-nozzle opening is formed. This cutting-nozzle element is inserted into a bone, if necessary held in a certain position via end spacers (not shown). By axial rotation of the cutting-nozzle body, with simultaneous discharge, a notch is produced in the bone, or the bone is even severed. So that the outflowing severing medium does not remain in the bone interior space, the corresponding shut-off element, which is provided inside the cutting-nozzle body, is designed as a hollow shaft and can draw the liquid out of the interior space of the bone. So that other uses for severing or removing bones are also possible, cutting-nozzle elements which have end nozzle openings are shown in other exemplary embodiments. These nozzle openings can also be opened and closed at a certain frequency, which is selectable, so that a pulsed water jet can be discharged.

A corresponding water-jet cutting system is equipped with an interchangeable supply reservoir of varying size, in which case the supply reservoir can essentially be connected to a pressure-generating device in an interchangeable manner. The pressure-generating device is preferably of electromechanical type and moves a linear drive onto a plunger element. As a result, a pressure which can be supplied to the cutting-nozzle element via a connecting line is generated in a pressure space. The supply reservoirs are preferably of a size which can be selected so as to vary and contain the severing medium with, if necessary, abrasive agents.

Only the cutting-nozzle element has to be cleaned after the operation. The supply reservoir is merely exchanged and can be recycled after use.

Furthermore, it is advantageous that such a water-jet cutting system is exceptionally small and can be produced cost-effectively, since any desired supply reservoir can be mounted on the pressure-generating device.

BRIEF DESCRIPTION OF THE DRAWINGS

Further advantages, features and details of the invention follow from the description below of preferred exemplary embodiments and with reference to the drawing, in which.

DETAILED DESCRIPTION

Figure 1:
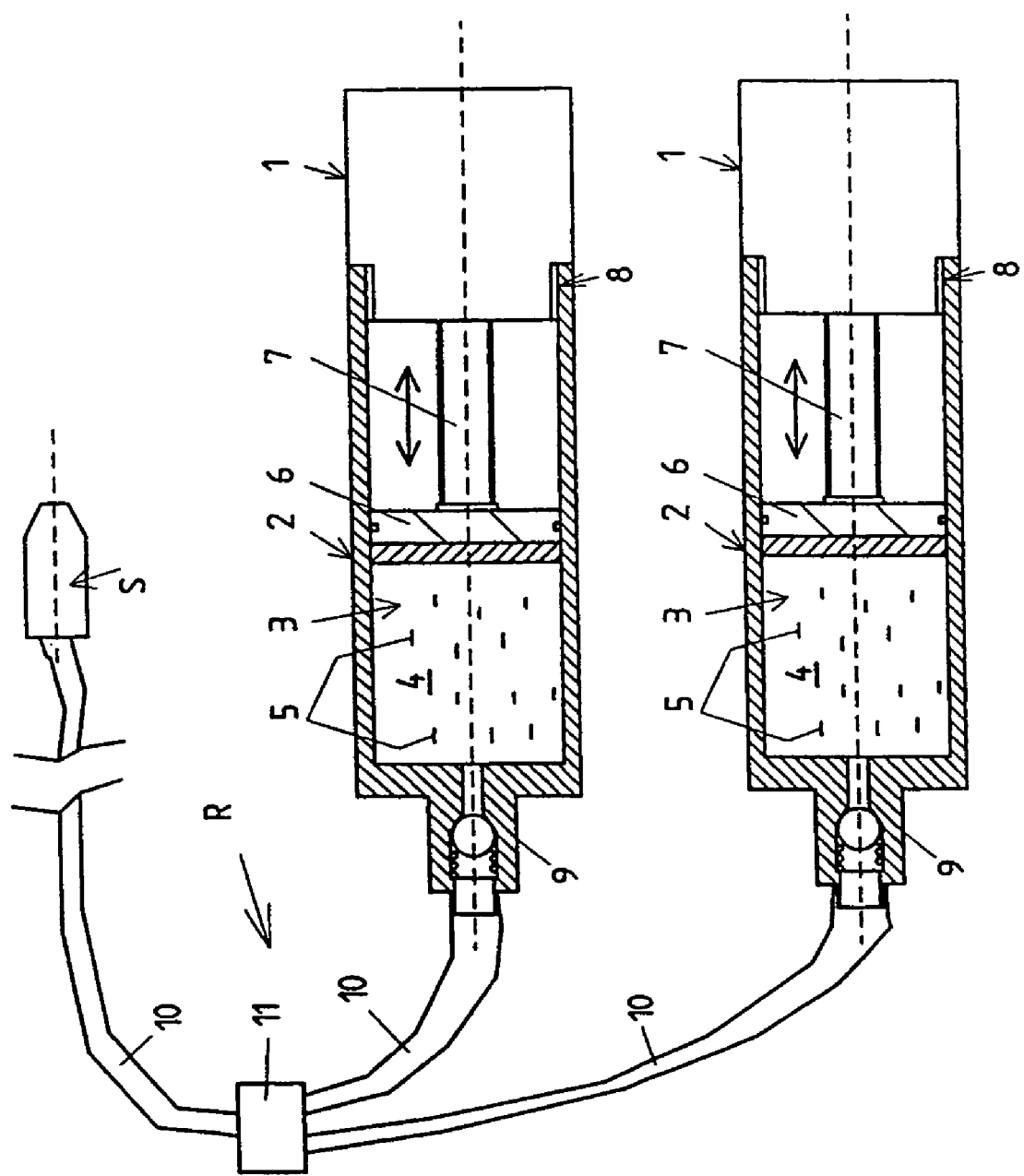
FIG. 1 shows a schematic plan view of a water-jet cutting system according to the invention with interchangeable supply reservoir.

According to FIG. 1, a water-jet cutting system R according to the invention for severing or removing a biological structure, in particular a human bone, has a pressure-generating device 1, adjoining which, preferably in an interchangeable manner, is a supply reservoir 2. The supply reservoir 2 has a pressure space 3 in which a severing medium 4 is introduced. The severing medium 4 is preferably sterile and aseptic water, which, if necessary, is enriched with abrasive agent 5. The abrasive agents 5 used may be inorganic or organic substances, such as, for example, sodium chloride, biological amino acids, monosaccharides and disaccharides and also sugars and alcohols. These abrasive agents 5 may also be supplied via injectors or the like (not shown here).

The supply reservoir 2 is closed by means of a plunger element 6, which can be actuated via a linear drive 7 of the pressure-generating device 1. The linear drive 7 is preferably an extendable mechanical spindle which can be driven in particular as an electromechanically operated linear actuator of the pressure-generating device 1. Via gearing and things such as drive elements (not shown here), the spindle can be extended and can exert a very high pressure on the plunger 6. In this case, the supply reservoir 2 is supported on the pressure-generating device 1 via a quick-acting lock 8. The quick-acting lock 8 may be of the most varied type and have a threaded connection, a push-in connection, a bayonet lock or the like. There are no limits to the invention in this respect.

However, it is important that, after the severing medium 4 has been completely discharged from the pressure space 3 by moving the plunger element 6 in the direction of an outlet valve 9, the medium 4 is fed completely to the cutting-nozzle element S via a connecting line 10. The severing medium 4 is discharged there radially or axially under very high pressure.

The outlet valve 9 is preferably designed as a check valve. This check valve is connected to the connecting line 10 such that it can be released again, in which case consideration may also be given to producing a releasable connection between outlet valve 9 and pressure-generating device 1.

The functioning of the present water-jet cutting system is as follows:

For the water-jet cutting, a severing medium under pressure, in particular in a pressurized manner is fed to the cutting-nozzle element S. To this end, the supply reservoir 2 is mounted on the pressure-generating device 1. The severing medium 4 is poured in. The supply reservoir 2 is then pressurized by being acted upon by the plunger 6 via the linear drive 7, so that the severing medium 4 can be fed completely to the cutting-nozzle element S via the connecting line 10. So that there is no idle time during the operation, when a supply reservoir is empty for example, a second pressure-generating device 1 having a second supply reservoir 2 may be provided, this second pressure-generating device 1 jointly feeding the severing medium 4 to the cutting-nozzle element S via a directional control valve 11. While the one supply reservoir is being emptied during the operation, the other supply reservoir can be exchanged.

From the present inventive idea, different supply reservoirs 2 which have capacities of different size for severing agents and which fit, for example, onto a single pressure-generating device 1 are also to be designed.

Figure 2:
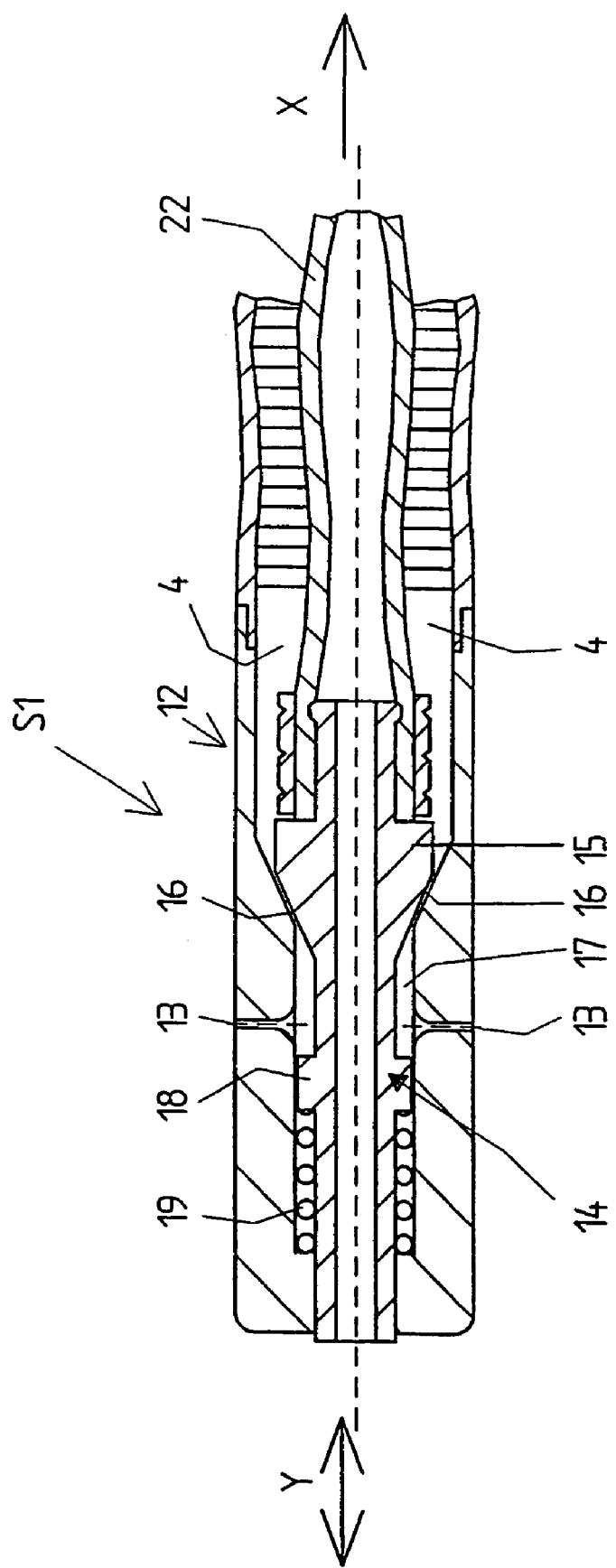
FIG. 2 shows a schematic partial longitudinal section through a cutting-nozzle element according to the invention.

Shown in FIG. 2 is a possible cutting-nozzle element $S_1$ which has a cutting-nozzle body 12 which is designed to be hollow in the interior. In the preferred exemplary embodiment, at least one nozzle opening 13 is provided radially, through which the severing medium 4 flows out under very high pressure for the severing, cutting or removal.

Provided inside the cutting-nozzle body 13 is a shut-off element 14 which is axially movable in a reciprocating manner, as shown in double arrow direction Y.

The shut-off element 14 forms a cone-like annular gap 16 via a cone 15 of the cutting-nozzle body 12, this cone 15 having a corresponding profile of the same kind.

Following the cone 15, the shut-off element 14 is of constricted design and forms an annular space 17 relative to the cutting-nozzle body 14, the severing medium 4 flowing outward out of this annular space 17 through the radial nozzle openings 13. A shaft shoulder 18 of the shut-off element 14 adjoins the annular space 17 and is connected to the cutting-nozzle body 12 on the inside virtually free of play. Adjoining the shaft shoulder 18, which also serves to center and axially guide the shut-off element 14, is an energy-storing element 19, which is supported at the end face on the shaft shoulder 18 and is supported on the other side at the end face on the cutting-nozzle body 12 on the inside. As a result, the shut-off element 14 is permanently deflected in an X-direction. The severing medium 4 flows through the annular gap 16 and is then discharged from the nozzle openings 13 under high pressure via the annular space 17.

However, it is important in the case of the present invention that a pulsating jet is produced from the nozzle openings 13 on account of a very small annular gap 16 in the region of the cone 15, the severing medium being greatly accelerated in this annular gap 16. This produces a vacuum which further reduces the annular gap 16 until severing medium 4 no longer flows. As a result, the shut-off element 14 is moved against the X-direction shown. The energy-storing element 19 is thereby loaded and applies pressure to the shut-off element 14. The latter yields to the pressure of the energy-storing element 19 and causes the shut-off element 14 to move in the X-direction shown, so that the severing medium 4 can again flow out through the widened annular gap 16, the adjoining annular space 17 and thus through the nozzle opening 13. This action repeats itself.

A pulsation can be controlled or set on the basis of pressures which can be set in a varying manner and on the basis of selectable energy-storing elements 19 and different geometries of the annular gap 16. This pulsation serves essentially to sever bones and tissue parts. It has proved to be especially favorable to use the pulsation. Tissue structures which must not be damaged, such as the periosteum for example, are moved only within the elastic range by a pulsating jet. The pulsed jet then removes or severs the biological structure, in particular the bone. This ensures that periosteum or other soft tissue is attacked or damaged only slightly during the severing of bone.

A tube element 22, which is preferably of elastic type, adjoins the shut-off element 14. It permits an axial movement of the shut-off element 14 in the Y-direction shown. At the same time, it serves to draw off severing medium 4 which is located in the bone interior when the cutting-nozzle element $S_1$ is inserted into a bone interior space.

Figure 3:
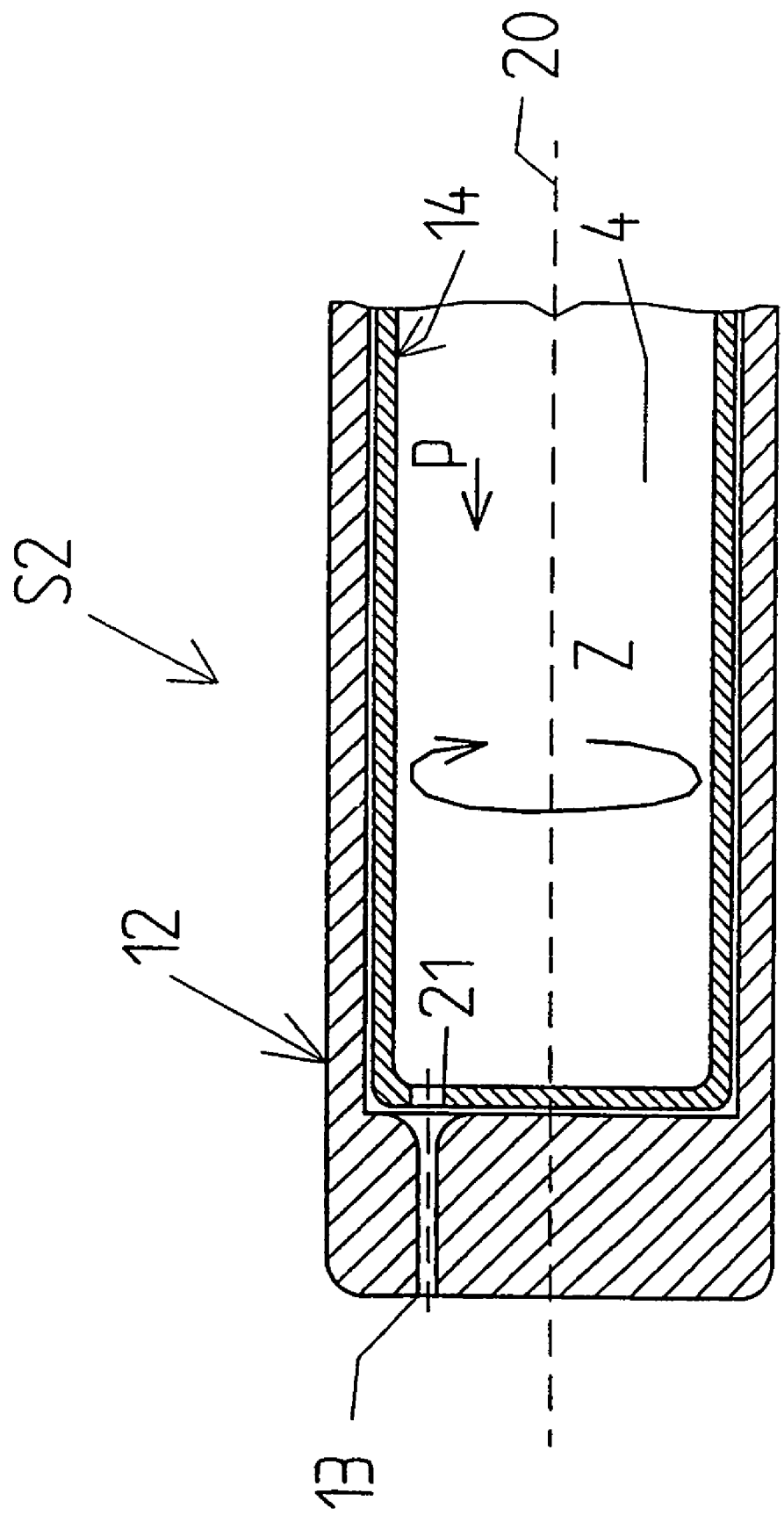
FIG. 3 shows a partial longitudinal section through a further exemplary embodiment of a further cutting-nozzle element.

Shown in a further exemplary embodiment of the present invention according to FIG. 3 is a cutting-nozzle element $S_2$ in which the nozzle opening 13 is provided axially at the end face in the cutting-nozzle body 12. A shut-off element 14 is inserted as hollow shaft inside the cutting-nozzle body 12 of hollow design and is rotatable about an axis 20 in the Z-direction shown. A discharge opening 21 is provided at the end face in the shut-off element 14 of hollow design, which fits precisely into the cutting-nozzle body 12, the discharge opening 21 coinciding with the nozzle opening 13 in a certain position. However, the provision of a multiplicity of discharge openings 21 at the end face is also intended to be within the scope of the present invention, so that, when the shut-off element 14 is rotated, the severing medium 4, which is introduced inside the shut-off element 14 under high pressure, discharges outward in a pulsating manner via the discharge opening 21 and when the latter coincides with the nozzle opening 13. The pulsation or the cyclical discharge of severing medium 4 from the nozzle opening 13 can be influenced by the number of corresponding discharge openings 21 or by the rotational speed of the shut-off element 14 about an axis 20. The rotation may be effected in any desired manner, mechanically, electromechanically or some other way.

Figure 4:
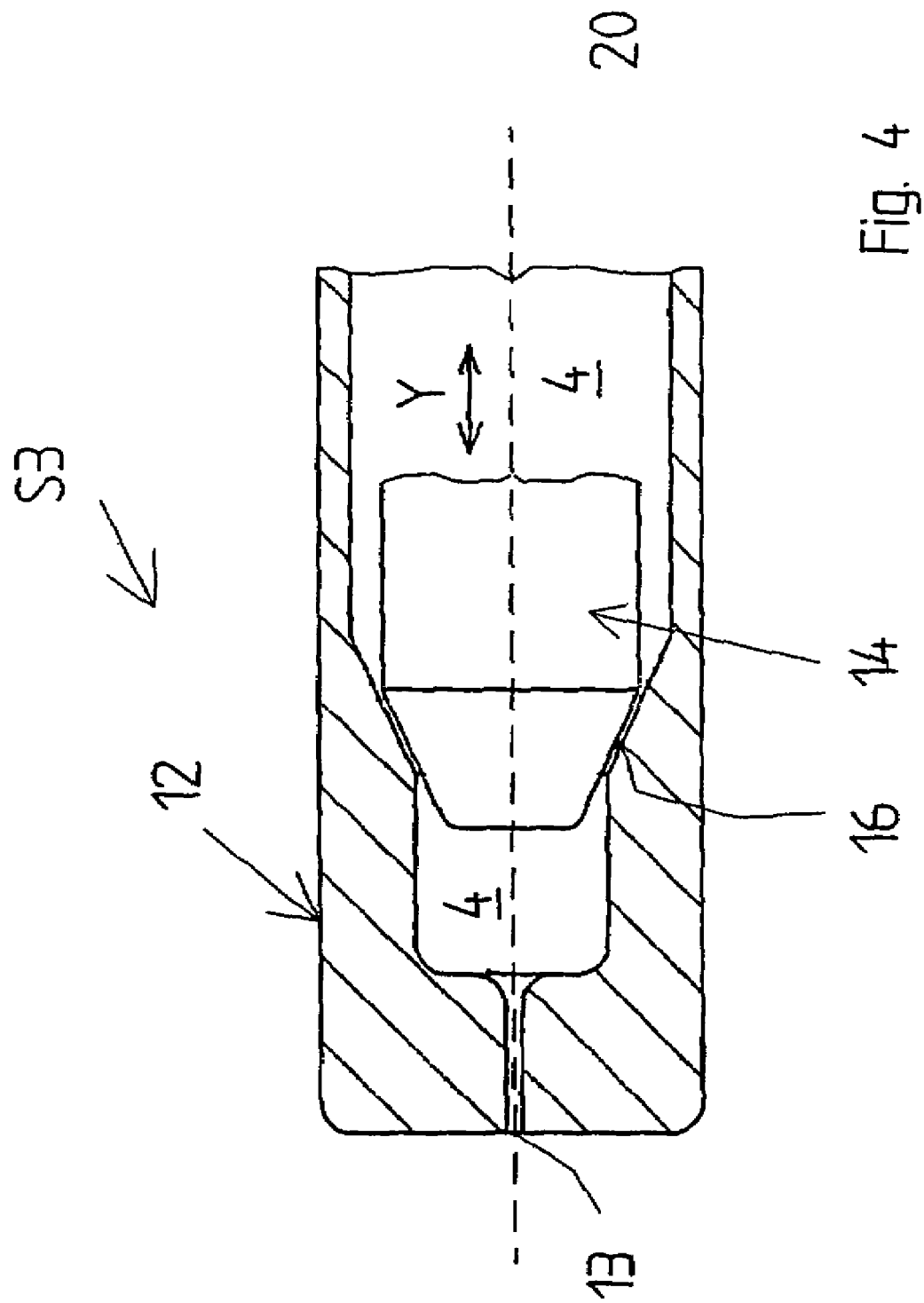
FIG. 4 shows a schematic partial longitudinal section through a further exemplary embodiment of the cutting-nozzle element.

Shown in the last exemplary embodiment of the present invention according to FIG. 4 is a cutting-nozzle element $S_3$ in which the cutting-nozzle body 12 is designed to be hollow and has a nozzle opening 13 at the end face in the region of an axis 20.

The shut-off element 14 sits in an axially movable manner inside the cutting-nozzle body 12 and is of conical design and engages in a correspondingly formed cone of the cutting-nozzle body 12. The severing medium 4 flows between shut-off element 14 and the interior space of the cutting-nozzle body 12 when the annular gap 16 is open. The annular gap 16 is opened and closed by a translatory axial movement of the shut-off element 14 in double arrow direction Y shown. This movement may be produced, for example, mechanically, electromechanically or even by a piezoelectric element. Many different possibilities which are intended to fall within the scope of the invention are conceivable here.

The invention claimed is:

1. A cutting-nozzle element for severing or removing a biological structure when the cutting-nozzle element is fed with a fluid under pressure, comprising a hollow cutting-nozzle body having a longitudinal axis, the hollow cutting-nozzle body receives a shut-off element which is movable within the hollow cutting-nozzle body in a reciprocating manner along the longitudinal axis wherein the hollow cutting-nozzle body defines with the shut-off element an annular space, at least one nozzle extending radially with respect to the longitudinal axis and communicating with the annular space, and further including means for reciprocating the shut-off element to provide a pulsed feed of fluid under pressure to the at least one radial nozzle.

2. An element according to claim 1, wherein the means for reciprocating comprises (1) a biasing means for moving the shut-off element in a first direction and (2) means for selectively moving the shut-off element in a second direction opposite the first direction for feeding fluid under pressure in a pulsed manner to the annular space.

3. An element according to claim 2, wherein the means for selectively feeding comprises a variable gap formed between a surface of the shut off element and an inner wall of the cutting-nozzle body.

4. An element according to claim 3, wherein the means for selectively moving the shut-off element in the second direction comprises a motor means which receives fluid under pressure via the variable gap.

5. An element according to claim 4, wherein the fluid motor means comprises a shoulder on the shut-off element which has a first surface which is acted on by the fluid under pressure.

6. An element according to claim 5, wherein the shoulder has a second surface which is acted on by the biasing means in opposition to the first surface.

7. An element according to claim 1, wherein the shut-off element has an internal passage for removing the fluid and biological structure.

* * * * *